(12) United States Patent
Yamshchikov

(10) Patent No.: US 7,459,163 B2  
(45) Date of Patent: *Dec. 2, 2008

(54) INFECTIOUS DNA AS A VACCINE AGAINST WEST NILE AND OTHER FLAVIVIRUSES

(75) Inventor: Vladimir F. Yamshchikov, Olathe, KS (US)

(73) Assignee: University of Kansas, Lawrence, KS (US)

( * ) Notice: Subject to any disclaimer, the term of this patent is extended or adjusted under 35 U.S.C. 154(b) by 120 days.

This patent is subject to a terminal disclaimer.

(21) Appl. No.: 11/065,783

(22) Filed: Feb. 25, 2005

(65) Prior Publication Data

US 2005/0276816 A1    Dec. 15, 2005

Related U.S. Application Data

(60) Provisional application No. 60/547,503, filed on Feb. 25, 2004.

(51) Int. Cl.
*A61K 39/12* (2006.01)
*A61K 48/00* (2006.01)
*C12N 7/01* (2006.01)
*C12N 15/86* (2006.01)
*C12N 5/10* (2006.01)

(52) U.S. Cl. .............. 424/218.1; 435/235.1; 435/320.1; 435/325; 514/44

(58) Field of Classification Search .................. 435/6, 435/5, 226; 424/199.1, 85.1, 204.1, 205.1
See application file for complete search history.

(56) References Cited

OTHER PUBLICATIONS

Pugachev et al., "New developments in flavivirus vaccines with special attention to yellow fever," Curr Opin Infect Dis 18:387-394 (2005).*

Drebot et al., "West Nile Virus: Update for family physicians," Can Fam Physician 51:1094-1099 (2005).*

Lodish et al. "Molecular Cell Biology," Second Printing, Scientific American Book, pp. 120-121 (1995).*

Shi et al., "Infectious cDNA Clone of the Epidemic West Nile Virus from New York City," Journal of Virology, vol. 76, No. 12 (pp. 5847-5856) (2002).*

Lustig et al (Viral Immunology 13:401-410, 2000).*

Yamschikov et al (Virology 281:294-304, 2001).*

Yamschikov et al (Virology 272-280, 2001).*

Yamshchikov, V.F., Wengler, G., Perelygin, A.a., Brinton, M.A., Compans, R.W., 2001. An infectious clone of the West Nile flavivirus. Virology 281 (2), 294-304.

Yamshchikov, V.F., Mishin, V. P., Cominelli, F., 2001. A new strategy in design of +RNA virus infectious clones enabling their stable propagation in *E. coli.* Virology 281, 272.

Yamshchikov, G., Borisevich, V., Seregin, A., Chaporgina, E., Mishina M., Mishin, V., Wai Kwok, C., Yamshchikov, V.F., 2004. An attenuated West Nile prototype virus is highly immunogenic and protects against the deadly NY99 strain: a candidate for live WN vaccine development. Virology 330, 304-312.

Mishin, V.P., Cominelli, F., Yamshchikov, V.F., 2001. A 'minimal' approach in design of flavivirus infectious DNA. Virus Research 81, 113-123.

* cited by examiner

*Primary Examiner*—Mary E Mosher
(74) *Attorney, Agent, or Firm*—Stinson Morrison Hecker LLP (57) ABSTRACT

A vaccine for West Nile virus that protects a subject against West Nile infection comprising an a pharmaceutically acceptable carrier and a therapeutically effective dose of an infectious agent selected from the group consisting of: a live attenuated infectious (+) RNA virus designated as WN1415, a vector comprising infectious DNA encoding an infectious (+) RNA molecule encoding the West Nile virus, and the West Nile (+) RNA virus designated as WN956D117B3 (GenBank #M12294).

19 Claims, 2 Drawing Sheets

SEQUENCE LISTING

```
<160> NUMBER OF SEQ ID NOS: 1

<210> SEQ ID NO 1
<211> LENGTH: 10962
<212> TYPE: DNA
<213> ORGANISM: West Nile virus
<300> PUBLICATION INFORMATION:
<308> DATABASE ACCESSION NUMBER: GenBank/M12294
<309> DATABASE ENTRY DATE: 2002-05-08
<313> RELEVANT RESIDUES IN SEQ ID NO: (1)..(10962)

<400> SEQUENCE: 1
agtagttcgc ctgtgtgagc tgacaaactt agtagtgttt gtgaggatta acaacaatta      60
acacagtgcg agctgtttct tggcacgaag atctcgatgt ctaagaaacc aggagggccc     120
ggtaaaaacc gggctgtcaa tatgctaaaa cgcggtatgc cccgcggatt gtccttgata     180
ggactaaaga gggctatgct gagtctgatt gacgggaagg gcccaatacg tttcgtgttg     240
gctcttttgg cgttttttcag attcactgca atcgctccga ctcgtgcggt gctggacaga     300
tggagaggcg tcaacaaaca aacagcaatg aagcatctct tgagtttcaa gaaagaacta     360
ggaactctga ccagtgccat caaccgccgg agcacaaaac aaaagaaaag aggaggcaca     420
gcgggcttta ctatcttgct tgggctgatc gcctgtgctg gagctgtgac cctctcgaac     480
ttccagggca aagtgatgat gacagtcaat gcaaccgatg tcactgacgt gattaccatt     540
ccaacagctg ctgggaaaaa cctgtgcatc gtaagggcta tggacgtagg atacctttgt     600
gaggatacta tcacttatga atgtccggtc ctagctgctg gaaatgaccc tgaagacatt     660
gactgctggt gcacgaaatc atctgtttac gtgcgctatg gaagatgcac aaaaactcgg     720
cattcccgtc gaagcagaag gtctctgaca gtccagacac atggagaaag tacactggcc     780
aacaagaaag gagcttggtt ggacagcaca aaagccacga gatatctggt gaagacagaa     840
tcatggatac tgagaaaccc gggctacgcc ctcgttcag ctgtcattgg atggatgcta     900
ggaagcaaca caatgcaacg cgtcgtgttt gccattctat tgctcctggt ggcaccagca     960
```

```
tacagcttca actgtttagg aatgagtaac agagacttcc tggagggagt gtctggagct    1020
acatgggttg atctggtact ggaaggcgat agttgtgtga ccataatgtc aaaagacaag    1080
ccaaccattg atgtcaaaat gatgaacatg aagcagcca acctcgcaga tgtgcgcagt     1140
tactgttacc tagcttcggt cagtgacttg tcaacaagag ctgcgtgtcc aaccatgggt    1200
gaagcccaca acgagaaaag agctgacccc gccttcgttt gcaagcaagg cgttgtggac    1260
agaggatggg gaaatggctg cggactgttt ggaaggggga gcattgacac atgtgcgaag    1320
tttgcctgta caaccaaagc aactggatgg atcatccaga aggaaaacat caagtatgag    1380
gttgccatat ttgtgcatgg cccgacgacc gttgaatctc atggcaagat aggggccacc    1440
caggctggaa gattcagtat aactccatcg gcgccatctt acacgctaaa gttgggtgag    1500
tatggtgagg ttacggttga ttgtgagcca cggtcaggaa tagacaccag cgcctattac    1560
gttatgtcag ttggtgagaa gtccttcctg gttcaccgag aatggtttat ggatctgaac    1620
ctgccatgga gcagtgctgg aagcaccacg tggaggaacc gggaaacact gatggagttt    1680
gaagaacctc atgccaccaa acaatctgtt gtggctctag gtcgcaggaa aggtgcgttg    1740
caccaagctc tggccggagc gattcctgtt gagttctcaa gcaacactgt gaagttgaca    1800
tcaggacatc tgaagtgtcg ggtgaagatg gagaagttgc agctgaaggg aacaacatat    1860
ggagtatgtt caaaagcgtt caaattcgct aggactcccg ctgacactgg ccacggaacg    1920
gtggtgttgg aactgcaata ccggaaca gacggtccct gcaaagtgcc catttcttcc     1980
gtagcttccc tgaatgacct cacacctgtt ggaagactgg tgaccgtgaa tccatttgtg    2040
tctgtggcca cagccaactc gaaggttttg attgaactcg aaccccgtt tggtgactct    2100
tacatcgtgg tgggaagagg agaacagcag ataaaccatc actggcacaa atctgggagc    2160
agcattggaa aggcctttac caccacactc agaggagctc aacgactcgc agctcttgga    2220
gatactgctt gggattttgg atcagttgga ggggttttca cctcagtggg gaaagccata    2280
caccaagtct ttggaggagc ttttagatca ctctttggag ggatgtcctg gatcacacag    2340
ggacttctgg gagctcttct gttgtggatg ggaatcaatg cccgtgacag gtcaattgct    2400
atgacgtttc ttgcggttgg aggagttttg ctcttccttt cggtcaacgt ccatgctgac    2460
acaggctgtg ccattgatat tggcaggcaa gagctccggt gcggaagtgg agtgtttatc    2520
cacaacgatg tggaagcctg gatggatcgt tacaagttct acccggagac gccacagggc    2580
ctagcaaaaa ttatccagaa agcacatgca aaggagtct gcggcttgcg ttccgtttcc     2640
agactcgagc accaaatgtg ggaagccatt aaggatgagc tgaacaccct gttgaaagag    2700
aatggagtcg acttgagtgt cgtggtggaa aaacagaatg ggatgtacaa agcagcacca    2760
aaacgtttgg ctgccaccac cgaaaaactg gagatggggt tggaaggcttg gggcaagagt    2820
atcatctttg cgccagaact agctaacaac accctttgtca tcgacggtcc tgagactgag    2880
gaatgcccaa cggccaaccg agcatggaac agtatggagg tagaggactt tggatttgga    2940
ctgacaagca ctcgcatgtt cctgaggatt cgggaaacga acacaacgga atgcgactcg    3000
aagatcatag gaaccgccgt caagaacaac atggctgtgc atagtgatct atcatactgg    3060
atagagagcg gactcaacga cacctggaag cttgagaggg cggttctagg agaagtcaaa    3120
tcatgcacct ggccagaaac ccacactctg tggggtgatg gagttctgga aagtgatctc    3180
atcatacccca tcaccttggc aggacccaga agcaaccaca acaggagacc agggtacaaa    3240
actcagaacc aaggcccatg ggatgagggg cgcgtcgaga ttgactttga ctattgccca    3300
```

```
ggaacaacag taactataag tgacagttgc gaacaccgtg gacctgcggc acgcacaacc    3360
actgagagtg ggaagctcat cacagactgg tgctgcagaa gttgcaccct ccctccactg    3420
cgcttccaga ctgagaatgg ctgttggtat ggaatggaaa ttcgacctac gcggcacgac    3480
gaaaagaccc tcgtgcaatc gagagtgaat gcatacaacg ccgacatgat tgatcctttt    3540
cagttgggcc ttatggtcgt gttcttggcc acccaggagg tccttcgcaa gaggtggacg    3600
gccaagatca gcattccagc tatcatgctt gcactcctag tcctagtgtt tgggggtatt    3660
acgtacactg atgtcctgcg atatgtcatt ctcgtcggcg ccgcgtttgc tgaagcaaac    3720
tcaggaggag acgtcgtgca cttggcactt atggctacat tcaagattca accagtcttt    3780
ctggtggctt ccttttttgaa ggcaaggtgg accaaccaag agagtatttt gctcatgctt    3840
gcagctgctt tcttccaaat ggcttactat gacgccaaga atgttctgtc atgggaagtg    3900
cctgacgttt tgaactctct ctccgttgcg tggatgattc tcagagctat aagcttcacc    3960
aacacttcaa atgtggtggt gccgctgctg ccccttttga cacctggatt gaaatgctta    4020
aaccttgatg tgtacagaat tttgctactc atggttggag ttggaagcct catcaaagaa    4080
aaaaggagct ctgcagcaaa aaagaaagga gcttgcctca tctgcctagc gctggcgtct    4140
acaggagtgt tcaatccaat gatacttgca gctgggctaa tggcttgcga ccccaaccgc    4200
aagcggggct ggcctgctac agaagtgatg actgcagttg gactcatgtt tgccatcgtt    4260
gggggtctgg cagaacttga catagattct atggctatcc ccatgaccat cgccggactt    4320
atgttcgcgg catttgtcat ctctggaaag tcaacagaca tgtggattga gaggacggct    4380
gacattactt gggagagtga tgctgaaatc acaggctcta gcgaaagagt agatgtgagg    4440
ctggatgatg atggaaattt tcaactgatg aatgaccccg gggcaccatg gaaaatttgg    4500
atgcttagga tggcctgcct ggcgataagt gcctacacac cttgggcaat tctcccctcg    4560
gtcatcggat tctggataac ccttcagtac acaaagagag gaggtgttct ttgggacaca    4620
ccatcaccca aggagtacaa gaagggtgat accaccactg gcgtttacag aatcatgact    4680
cgaggtctgc ttggcagtta ccaagctgga gccggagtga tggtagaggg ggtgttccac    4740
acactatggc acaccactaa gggagctgct ctcatgagtg gtgagggacg tctggatccc    4800
tactggggga gcgtgaaaga ggaccgactt tgctatgggg ggccatggaa actccaacat    4860
aaatggaatg gacatgatga ggtccaaatg attgtcgtgg agccagggaa aaatgtgaaa    4920
aacgtccaga ccaagcccgg agtgtttaag acaccagaag gagaaattgg ggcagttacg    4980
ctagactatc ctaccggaac gtcaggttcc cccattgtag acaaaaatgg agatgtgatt    5040
ggattgtatg gaacggcgt catcatgcct aatggttcat acataagcgc cattgtgcaa    5100
ggagagagaa tggaagaacc ggcaccagct ggcttcgaac tgaaatgtt gaggaagaaa    5160
cagatcactg tccttgatct gcaccccgga gcaggaaaga cacgcaagat acttccccaa    5220
atcatcaagg aggccatcaa caaaagattg aggacggctg tgctggcacc caccagggtc    5280
gttgctgctg agatgtctga ggccctgaga ggacttccca ttcggtacca aacctcagca    5340
gtgcacagag agcacagtgg aaatgagatc gttgatgtca tgtgccatgc cacccctcaca    5400
cacaggctga tgtctccaca cagagtcccc aactacaacc tgttcataat ggatgaagcc    5460
catttcacgg atccagcgag catcgcagcc agagatacaa tagcaaccaa ggttgaattg    5520
ggcgaagccg ccgcgatttt catgacggca acgccacccg ggacttctga ccccttccca    5580
gagtctaatg ctcctatctc ggacatgcaa acagagatcc cagacagagc ctggaacact    5640
ggatatgaat ggataactga gtatgttgga aagaccgttt ggtttgttcc aagtgtgaaa    5700
```

```
atgggaaatg agattgccct ctgtctgcaa cgggcgggga agaaggttat ccagctgaac    5760
agaaagtcct atgagacaga gtaccccaag tgtaagaacg atgattggga ttttgtcatc    5820
accacagaca tatcagaaat gggagccaac ttcaaggcga gcagagtgat cgacagccgc    5880
aaaagcgtga acccaccat cattgaggaa ggtgatggaa gagtcatcct ggggggaaccc    5940 tcagccatca cggctgccag cgctgctcag cggagaggac cataggaag aaacccatca    6000 caagttggtg atgagtattg ctatggaggg cacacaaatg aggatgattc caactttgct    6060
cactggacag aggctcgcat catgctagac aacatcaaca tgccgaatgg tctggtggct    6120
caactatatc agcctgagcg cgagaaggtg tacaccatgg acggggaata caggctcaga    6180
ggggaagaac ggaagaactt ccttgaattc ctgagaacag ctgatttacc agtctggctc    6240
gcttacaaag tggcagcagc aggaatatca taccatgacc ggaaatggtg ctttgatgga    6300
cctcgaacca acacgattct tgaagacaac aatgaagttg aagtcatcac gaagttgggt    6360
gagagaaaga tcctaagacc caggtgggca gatgctagag tgtactcaga ccatcaagct    6420
ctaaagtcct tcaaagattt tgcatcgggg aaacgatcac aaatcgggct cgttgaggtg    6480
ctcgggagaa tgcctgaaca cttcatggtg aaaacttggg aggcattgga cacgatgtat    6540
gtggtggcga ccgctgaaaa aggaggccga gctcacagga tggctcttga ggagctaccg    6600
gacgcccttc agacaatagt tttgattgca ctattgagtg tgatgtcctt aggtgtgttt    6660
tttctactca tgcaaaggaa gggcattggt aagattggct tgggaggagt aatcttagga    6720
gctgccacat tcttctgctg gatggctgaa gtcccaggaa cgaaaatagc aggcatgctc    6780
ctgctttccc tgctgctcat gattgttttg attccggagc cggaaaagca gcgctcacag    6840
actgataacc agctcgccgt gttcttgatc tgtgtgctca cactggtcgg cgccgtggct    6900
gccaatgaaa tgggctggct ggacaagacc aagaatgaca ttggcagcct gttggggcac    6960
aggccagaag ctagagagac gaccctggga gttgagagct tcttacttga tctgcggccg    7020
gccacggcat ggtcgctcta tgccgtaacg acagccgttc tcacccttt gctgaagcat    7080 ctaatcacgt cagactacat caacacttcg ttgacctcaa taaacgtcca agccagcgcg    7140
ttgttcactt tggccagagg cttccctttt gtggacgttg gtgtgtcagc tctcttgctg    7200
gcggtcgggt gctggggtca ggtgactctg actgtgactg tgactgcagc tgctctgctc    7260
ttttgccact atgcttacat ggtgccaggc tggcaagcgg aagccatgcg atctgcccag    7320
cggcggacag ctgctggcat catgaaaaat gtagtggtgg atgggatcgt ggccactgat    7380
gtacctgaac ttgaacgaac aactccagtc atgcagaaaa aagttggaca gatcatattg    7440
atcttggtat caatggccgc ggtggtcgtc aatccatcag tgagaaccgt cagagaggcc    7500
ggaattctga ctacagcagc agcagtcacc ctatgggaga atggtgctag ttcagtgtgg    7560
aatgcaacga cagctattgg cctttgtcac atcatgcgag aggatggct ctcgtgtctc    7620 tccatcatgt ggactctcat caaaaacatg gagaaaccag gcctcaagag gggtggagcc    7680
aaaggacgca cgctagggga agtttggaag gagagactca accacatgac gaaggaagaa    7740
tttaccagat acagaaaaga agccatcact gaagttgacc gctccgcagc aaaacatgct    7800
aggagagagg gaaacatcac tggaggccac ccagtctcac ggggaaccgc gaaattacgg    7860
tggttagtgg aaaggcgttt cctcgagcca gtgggaaagg ttgtggatct cgggtgtggt    7920
agaggcggct ggtgctatta catggctacc cagaagaggg tacaggaagt gaaagggtac    7980
acgaaaggag gacctggcca tgaagaacca caactggtgc agagctatgg ttggaatatt    8040
```

```
gttaccatga agagtggagt cgacgtcttc tacagaccat cagaagcgag cgacacactg    8100
ctctgtgaca ttggagagtc atcgtcaagt gccgaggtag aagaacaccg caccgtccgt    8160
gtcctggaga tggtggaaga ttggttgcac agaggaccga aggaattctg catcaaagtg    8220
ctatgccctt acatgcccaa agtgattgag aagatggaaa cactccaaag gcgatatgga    8280
ggtggcctta taagaaaccc cctttcacgc aactctaccc atgagatgta ctgggtgagc    8340
cacgcttcag gcaatatcgt ccactccgtc aacatgacaa gccaggtgct tctggggagg    8400
atggaaaaga aaacatggaa gggacccccag tttgaggaag atgtcaactt gggaagtgga    8460
acgcgggcag tagggaagcc tctcctcaat tctgatacta gcaagatcaa gaaccgaatt    8520
gagaggctga agaaagaata cagctccaca tggcaccagg atgcgaacca cccctacagg    8580
acctggaact accacggaag ctatgaagtg aaaccaaccg gctcagccag ctcccttgtg    8640
aatggggtag tcagattact ctcaaaacca tgggacacta tcaccaatgt gaccacgatg    8700
gccatgacag acaccactcc tttcggtcaa caacgagtgt tcaaggaaaa ggtggacaca    8760
aaggctccag agcctccaga aggagtcaaa tacgtcctca atgagaccac gaactggctg    8820
tgggcttttt tagcccgcga taagaaaccc aggatgtgtt cccggagga atttattgga    8880
aaagtcaaca gtaatgccgc cctaggagcg atgtttgaag aacagaacca atggaagaac    8940
gcccgggaag ctgtagagga tccaaagttt tgggagatgg tggatgagga gcgtgaagcg    9000
catctccgtg agaatgcaa cacctgcatc tacaacatga tgggaaagag agagaagaag    9060
cctggagagt tcggcaaagc taaaggcagc agagccatct ggttcatgtg gctggggcc    9120
cgcttcctgg agtttgaagc tctcggattc ctcaatgaag accactggct gggtaggaag    9180
aactcaggag gaggagttga aggcttagga ctgcagaagc tcgggtacat cttgaaggaa    9240
gttggaacaa agcctggagg aaaggtttac gctgatgata ccgcaggctg ggacacacgc    9300
atcaccaaag ctgacctcga gaatgaagcg aaggttcttg aactgctgga tgagaaacat    9360
cgacgtttag cgcggtccat catcgagctc acataccgac acaaagtcgt gaaagtgatg    9420
aggccagcgg ccgacgggaa aactgtgatg gacgtcatct ctagagagga tcagagagga    9480
agcggtcagg tagtgactta cgccctgaac accttcacca atctagcagt tcagctggtc    9540
agaatgatgg agggggaggg ggtcattgga cccgatgatg ttgaaaaact gggaaaagga    9600
aaaggcccta aggtcagaac ctggctgttt gagaatggcg aggagcgtct cagtcgcatg    9660
gccgtcagcg gtgatgactg cgtggtgaaa cctttggacg accgcttcgc cacatcacta    9720
cacttcctaa atgctatgtc aaaggtccgc aaagacatcc aggaatggaa accctcgacg    9780
gggtggtatg actggcagca ggttccattc tgttcaaacc atttcacgga actgatcatg    9840
aaggacggca ggacgctggt ggtcccgtgt cgtgaccaag acgagttgat tggacgtgcc    9900
aggatctctc caggggctgg atggaatgtg cgcgacaccg cctgcctggc gaagtcatac    9960
gcgcagatgt ggctgctgct ttatttccac cgtagagacc tgagattgat ggccaatgcc   10020
atctgttccg ctgtgcctgc caactgggtt cccacagggc gtaccacttg gtcgatccac   10080
gcaaaaggag aatggatgac gacggaagac atgctcgcag tctggaacag agtgtggatt   10140
gaggagaatg agtggatgga agacaaaaca ccagttgaga ggtggagtga tgttccatac   10200
tctgaaagag agaggacat ttggtgtggc agtttgatcg gcacacgaac ccgcgccact   10260
tgggctgaaa atatccatgt ggcaatcaat caggtccgtt cagtgattgg agaagagaag   10320
tatgtggatt acatgagctc cttgaggagg tatgaagaca ccattgtagt ggaggacact   10380
gttttgtaaa agatagtatt atagttagtt tagtgtaaat aggatttatt gagaatggaa   10440
```

```
gtcaggccag attaatgctg ccaccggaag ttgagtagac ggtgctgcct gcggctcaac  10500
cccaggagga ctgggtgacc aaagctgcga ggtgatccac gtaagccctc agaaccgtct  10560
cggaaggagg accccacgtg ctttagcctc aaagcccagt gtcagaccac actttaatgt  10620
gccactctgc ggagagtgca gtctgcgata gtgcccagg tggactgggt taacaaaggc  10680
aaaacatcgc cccacgcggc cataaccctg gctatggtgt taaccaggga gaagggacta  10740
gaggttagag gagacccgc gtaaaaagt gcacggccca acttggctga agctgtaagc  10800
caagggaagg actagaggtt agaggagacc ccgtgccaaa aacaccaaaa gaaacagcat  10860
attgacacct gggatagact aggggatctt ctgctctgca caaccagcca cacggcacag  10920
tgcgccgaca taggtggctg gtggtgctag aacacaggat ct                     10962
```

INFECTIOUS DNA AS A VACCINE AGAINST WEST NILE AND OTHER FLAVIVIRUSES

CROSS-REFERENCE TO RELATED APPLICATIONS

The present invention claims the benefit of provisional patent application No. 60/547,503, filed on Feb. 25, 2004, which is incorporated by reference in its entirety.

STATEMENT REGARDING FEDERALLY SPONSORED RESEARCH OR DEVELOPMENT

The present invention was sponsored by the National Institute of Allergy and Infectious Disease Contracts No. AI049258 and AI052084 and World Health Organization V22/181/128, and the government may have certain rights in the invention.

BACKGROUND OF THE INVENTION

Flaviviruses are (+) RNA viruses that cause such diseases as West Nile fever ("WN"), dengue fever ("DEN"), yellow fever ("YF"), St. Louis encephalitis, Japanese encephalitis ("JE"), and tick-borne encephalitis ("TBE"). West Nile virus was first isolated over 60 years ago from the blood of a febrile patient (Smithburn et al., 1940), and is one of the most widespread flaviviruses worldwide. The virions of the West Nile fever virus are spherical particles with a diameter of 50 nm constituted by a lipoproteic envelope surrounding an icosahedric nucleocapsid containing a positive polarity, single-strand RNA. A single open reading frame ("ORF") encodes all the viral proteins in the form of a polyprotein. The cleaving and maturation of this polyprotein leads to the production of about ten different viral proteins. The structural proteins are encoded by the 5' part of the genome and correspond to the nucleocapsid designated C (14 kDa), the envelope glycoprotein designated E (50 kDa), the pre-membrane protein designated prM (23 kDa), the membrane protein designated M (7 kDa). The non-structural proteins are encoded by the 3' part of the genome and correspond to the proteins NS1 (40 kDa), NS2A (19 kDa), NS2B (14 kDa), NS3 (74 kDa), NS4A (15 kDa), NS4B (29 kDa), NS5 (97 kDa).

The West Nile virus is endemic to Africa and has been repeatedly registered in Europe and Asia for decades causing self-limiting epidemics and epizootics (Murgue et al., 2001; Savage et al., 1999). Recent introduction of the virus into the naïve environment of the North American continent (Lanciotti et al., 1999) had disastrous consequences both for wildlife and human population (Roehrig et al., 2002) and in a few years has developed into a nationwide epidemiological problem. In addition to hundreds of human mortality cases reported to the Centers for Disease Control (CDC, 2004), the virus imposes a substantial economical burden, especially on the equine industry (Anonymous, 2003).

Cell-mediated immune response plays an important role in virus clearance and in protection from the disease (Diamond et al., 2003; Shrestha and Diamond, 2004). Since flavivirus nonstructural proteins supply the majority of dominant T-cell peptide determinants (Co et al., 2002), cell-mediated response induced by chimeric flaviviruses are mostly to vector proteins. However, development of a live attenuated West Nile vaccine, which may have a better capability to elicit balanced humoral and cell-mediated immune responses, is hindered by the high virulence and pathogenicity of the NY99 strain circulating in the U.S. (Beasley et al., 2002; Roehrig et al., 2002).

Based on serological data and genetic characterization, West Nile viruses were subdivided into two distinct lineages (Berthet et al., 1997; Price and O'Leary, 1967). Viruses of lineage 1, which includes the highly virulent NY99 strain, are most widespread and often were found in association with epidemics or epizootics (Roehrig et al., 2002). Although a few strains with a high virulence were also found among lineage 2 representatives (Beasley et al., 2002), viruses of this lineage have not been associated with disease outbreaks (Lanciotti et al., 1999). For this reason, lineage 2 viruses may be more attractive for development of live attenuated West Nile vaccine.

Modern (+) RNA virus studies increasingly rely on the infectious clone methodology, which allows for targeted manipulation of viral genomes. In the "classical approach", (+) RNA viruses are recovered from cells transfected with synthetic RNA made by in vitro transcription of infectious clone cDNA templates. In a layered DNA/RNA approach, also known as "infectious DNA," the infectious (+) RNA viruses are recovered directly after transfection of plasmids carrying viral genome cDNA into susceptible cells. Unfortunately, difficulties are often encountered in the design of flavivirus infectious DNA. Few studies have reported on the use of such infectious DNA construct as a vaccine.

The present invention is directed to the isolation of a virus useful for development of a West Nile vaccine. Isolate 956D117B3 (earlier also referred to as WN-Nigeria or WN-Wengler (Berthet et al., 1997; Lanciotti et al., 1999)) is a descendant of the West Nile virus prototype B956 (Smithburn et al., 1940), and is one of the first flaviviruses for which the complete nucleotide sequence has been determined (Castle et al., 1986; Castle et al., 1985; Wengler et al., 1985; GenBank #M12294). Earlier, the first West Nile infectious clone designed on the basis of the isolate 956D117B3 (Yamshchikov et al., 2001) was reported. While the virus was produced, the viral population was not characterized. In the present invention, it was demonstrated for the first time that the virus recovered from the molecular clone is highly attenuated, induces vigorous and balanced immune response and even at low doses protects mice against the virulent NY99 strain. Combined with its stable genotype and excellent growth characteristics in tissue culture, the recovered virus is well-suited for the development of veterinary and human live West Nile vaccines.

BRIEF SUMMARY OF THE INVENTION

An object of the present invention is to provide a (+) RNA viral material formed by infectious DNA.

Still another object of the present invention is to provide plasmid DNA encoding for an (+) RNA viral genome, which can be amplified in *E. coli* and easily prepared in large amounts.

Another object of the present invention is to use DNA immunization methodology for direct vaccination using infectious DNA, which will provide a stable and safe vaccine for an (+) RNA virus with increased shelf life due to a higher stability of the purified DNA.

Yet another object of the present invention is to provide a West Nile type 2 viral strain 956D117B3 and its WN1415 isolate that is immunogenic to type 1 viruses, such as the highly virulent NY99 strain.

Another object of the present invention is to provide a flavivirus infectious DNA that is dichotomous nature such that it is partially protective against its own infectivity. Although in cell culture higher inputs of infectious DNA correspond to higher infection rate, this results in decreased mortality even for a highly virulent virus.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 1 shows the cytopathic properties of the West Nile prototype strain B956 and the clonal isolate WN1415. Baby hamster kidney ("BHK") (top panel) or Vero (lower panel) monolayers were infected with 10-fold dilutions of corresponding viruses and incubated under 1% methylcellulose overlays for 4-5 days. Cells fixed with 1% HCHO were stained with Coumassie G250, washed, dried and photographed in visible light (left panels for each virus). Coumassie stain was removed with ethanol washes, and monolayers were rehydrated in 50% alcohol followed by PBS. Virus foci were immunostained as described in below and photographed in visible light (right panels for each virus).

FIG. 2 graphically shows the development of WN-specific IgG response. Four-week old NIH Swiss mice were immunized intramuscularly ("i.m.") with indicated doses of WN1415 and sera collected at three weeks post infection and at two weeks post challenge with 10 $LD_{50}$ of NY99. Serum samples were assayed by ELISA for WN-specific IgG using the NY99 viral antigen, and endpoint dilution values were averaged for survivors in each of the WN1415 dosage groups. Pre- and post-challenge IgG titers were compared using standard T-test. In the three highest WN1415 dosage groups mice did not display statistically significant changes in the titer of virus specific antibodies after the challenge ($p>0.05$), as compared to mice in the two lowest dosage group ($p<0.05$; see text for details).

FIG. 3 is a schematic drawing of WN infectious DNA pCMVWN. Abbreviations: WN genome cDNA—a cDNA copy of the complete West Nile virus genome; δ—hepatitis δ ribozyme sequence; TT—bovine growth hormone transcription termination and polyadenylation signal sequence; CMV—cytomegalovirus promoter/enhancer sequence; bla—ampicillin resistance gene; ori—pBR322 replication origin; i357—a 132 bp intron sequence inserted at pos. 357 of the WN genome. Individual elements are not drawn to scale.

DETAILED DESCRIPTION OF THE INVENTION

The present invention relates to a composition for eliciting an immune response or a protective immunity against West Nile virus. According to a related aspect, the present invention relates to a vaccine for preventing and/or treating a West Nile virus associated disease. As used herein, the term "treating" refers to a process by which the symptoms of a West Nile associated disease are ameliorated or completely eliminated. As used herein, the term "preventing" refers to a process by which a West Nile associated disease is obstructed or delayed. The compositions and vaccines of the invention comprises a live attenuated virus or an infectious DNA capable of producing a live attenuated virus. Most preferably, the live attenuated virus is produced in vivo using an "infectious DNA" approach.

As used herein, the term "immune response" refers to a T cells response or increased serum levels of antibodies to an antigen, or to the presence of neutralizing antibodies to an antigen, such as a West Nile polypeptide.

The term "protection" or "protective immunity" refers herein to the ability of the serum antibodies or T cell response induced during immunization to protect (partially or totally) against disease or death caused by the West Nile virus.

The methods of the invention comprise administering a composition having a therapeutically effective amount of a live attenuated West Nile virus or the infectious DNA encoding for the attenuated virus in an acceptable pharmaceutical carrier to the subject in need.

The "subject" or "patient" of the present invention is preferably an animal, e.g., such as mice, cows, pigs, horses, chickens, cats, dogs, etc., and is preferably a mammal, and most preferably human.

The term "therapeutically effective dose" or "therapeutically effective amount" means a dose or amount that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

The term "pharmaceutically acceptable" means approved by a regulatory agency of the federal or a state government or listed in the U.S. Pharmacopeia or other generally recognized pharmacopeia for use in animals, and more particularly, in humans.

The term "carrier" refers to a diluent, adjuvant, excipient, or vehicle with which the attenuated virus or infectious DNA is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

Thus, as used herein, the term "pharmaceutically acceptable carrier" means, but is not limited to, a vehicle for containing the DNA plasmid that can be injected into a mammalian host without adverse effects. Suitable pharmaceutically acceptable carriers known in the art include, but are not limited to, gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As discussed more fully below, in the present invention, the genetic material of West Nile virus type 2 strain 956D117B3 was rescued from archival RNA. Like many RNA viruses, a large heterogeneity exists within the viral population of 956D117B3, and the reported genome identifies the dominant quasispecies (GenBank #M11294, which is incorporated by reference). In the present invention, the 956D117B3 virus was used in the design of West Nile plasmid DNA construct. From the plasmid, a molecularly defined clonal variant designated WN1415 was isolated. WN1415 is significantly attenuated but remains highly immunogenic and protective in mice. As discussed more fully below, the immune responses developed upon infection with the substantially attenuated virus WN1415 protects mice against challenge with 100 times the lethal doses of West Nile NY99. The WN1415 clonal variant has $LD_{50}$ greater than $10^6$ pfu; yet immune responses developed after infection with much smaller doses of WN1415 protect mice against challenge with 100 $LD_{50}$ of the highly virulent NY99. Similar protection is achieved upon immunization with infectious DNA consisting of the genome of West Nile virus type 2 strain 956D117B3. While the reported genomes of both the 956D117B3 and the WN1415 isolate are substantially the same and differ only by two silent nucleotides, the heterogeneity of the viral population associated with the 956D117B3 strain makes it more pathogenic and virulent compared to the homogeneous WN1415 viral population as determined by present day sequencing technology.

Further, in the present invention, it was shown that West Nile infectious DNA, which is comprised of cDNA of the West Nile virus type 2 genome placed under transcriptional control of an eukaryotic promoter and inserted into a derivative of the pBR322 plasmid, initiates the flavivirus infectious cycle directly after transfection into susceptible cells or after inoculation in animals in vivo by intramuscular needle or needle-free injection, or by intradermal biolistic delivery. Due to the stability of supercoiled DNA plasmid and a high specific infectivity of the construct, West Nile infectious DNA is capable of initiating flavivirus infection even when used in very small amounts. Further, the protection achieved with the infectious construct is similar to that of WN1415.

Although West Nile infectious DNA as a plasmid carrying the full flavivirus genome controlled by eukaryotic transcription elements resembles a DNA vaccine, it is about 1000 to 10,000-fold more efficient in inducing antiviral protective immunity in mice via different inoculation routes.

It will be appreciated to those skilled in the art that the infectious DNA of the present invention may be formed using any suitable vector. In general, a vector is a nucleic acid molecule (typically DNA or RNA) that serves to transfer a passenger nucleic acid sequence (i.e., DNA or RNA) into a host cell. Three common types of vectors include plasmids, phages and viruses. Preferably, the vector is a plasmid. That is the infectious DNA vaccines of the present invention are comprised of DNA that is produced as a plasmid that can be introduced into animal tissue and therein is expressed by animal cells to produce a messenger ribonucleic acid (mRNA) molecule of the size of the flavivirus genome, which is translated to produce a viral polyprotein, that is processed by cellular machinery to provide a full set of flavivirus proteins that are capable to initiate replication of the above primary RNA transcript and thus initiate the virus replication cycle in animal tissue into which the above DNA plasmid was introduced.

Suitable and exemplary plasmid vectors that have been used in conventional DNA vaccines include, but are not limited to pBR322 (ATCC# 31344); pUC19 (ATCC# 37254); pcDNA3.1 (Invitrogen, Carlsbad Calif. 92008; Cat. NO. V385-20; pNGVL (National Gene Vector Laboratory, University of Michigan, Mich.); p414cyc (ATCC# 87380); p414GALS (ATCC# 87344), pBAD18 (ATCC# 87393), pBLCAT5 (ATCC# 77412), pBluescriptIIKS, (ATCC# 87047), pBSL130 (ATCC# 87145), pCM182 (ATCC# 87656), pCMVtkLUC (ATCC# 87633), pECV25 (ATCC#77187), pGEM-7zf (ATCC# 87048), pGEX-KN (ATCC# 77332), pJC20 (ATCC# 87113, pUB110 (ATCC# 37015), pUB18 (ATCC# 37253).

The infectious DNA of the present invention is also under the control of a suitable promoter. For eukaryotic expression, suitable vectors include the cytomegalovirus ("CMV") early promoter, or alternatively the Rous sarcoma virus ("RSV") LTR promoter, and the SV40 promoter.

The amount of plasmid present in the compositions or in the DNA vaccines of the present invention is preferably a therapeutically effective amount. A therapeutically effective amount of plasmid is that amount necessary so that the nucleotide sequence coding for the West Nile polypeptide performs its immunological role without causing overly negative effects in the host to which the composition is administered. The exact amount of plasmid to be used and the composition/vaccine to be administered will vary according to factors such as the strength of the transcriptional and translational promoters used, the type of condition being treated, the mode of administration, as well as the other ingredients in the composition. Preferably, the composition or the vaccine formulation is composed of from about 10 ng to about 1 μg of plasmid.

The immunogenicity of the DNA vaccine and pharmaceutical compositions of the present invention can also be modified by formulating with a pharmaceutically acceptable adjuvants or imunostimulants, such as alpha-interferon, beta-interferon, gamma-interferon, granulocyte macrophage colony stimulator factor ("GM-CSF"), macrophage colony stimulator factor ("M-CSF"), interleukin 2 ("IL-2"), interleukin 12 ("IL-12"), and CpG oligonucleotides. For preparing such compositions, methods well known in the art may be used.

Subcutaneous injection, intradermal introduction, impression through the skin, and other modes of administration such as intraperitoneal, intravenous, oral, or inhalation delivery are also suitable. For example, vectors containing the infectious DNA of the present invention can be introduced into the desired host by methods known in the art, for example, transfection, electroporation, microinjection, microparticles, microcapsules, transduction, cell fusion, DEAE dextran, calcium phosphate precipitation, lipofection (lyposome fusion), use of a gene gun (particle bombardment), or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

Administration may be single or multiple (i.e. single-dose or including a booster). Such administration may be alone or in combination with other active therapeutic agents against West Nile virus.

In the following examples, virus titers were determined by a microplate method. Serial 10-fold dilutions of virus stocks in DMEM containing 0.5% FCS were prepared in duplicate wells of a 96-well cluster and 50 μl was transferred in parallel to confluent monolayers of Vero cells in 96-well plates using a multichannel pipettor. The plates were incubated for 1 hour at 37° C. in the $CO_2$ incubator with occasional shaking. The inocula were aspirated, replaced with 100 μl of the growth medium, and plates returned to the incubator for additional 24 hours. Under these conditions, virus multiplication foci consisted of compact clusters of about 5-15 cells, which stained positive for the viral antigen as described below.

PRNT assays were done in a similar microplate format. Two-fold dilutions of immune sera in DMEM plus 0.5% FCS were mixed in duplicate in 96-well plates with equal volume of NY99 virus prediluted in the same medium to 2×10³ pfu/ml and the plate was kept in $CO_2$ incubator at 37° C. for 1 hour. Fifty microliters of each mix (containing about 50 pfu) was transferred in parallel into a 96-well plate with confluent Vero monolayers and incubated for another hour as above. The inocula were aspirated, replaced with 100 μl of the growth medium and plates returned to the incubator for 24 hours.

At the end of the incubation period, cells were fixed by addition of 25 μl/well of 10% formalin in PBS and incubation for 30 minutes at room temperature. Foci of viral multiplication were visualized on fixed monolayers with DAB substrate (Vector Laboratories, Burlingame, Calif.) after the following treatment sequence (50 μl/well): 0.5% Thesit (Sigma-Aldrich) for 10 minutes, 1:1000 dilution of WN mouse hyperimmune antiserum for 30 minutes, 1:1000 dilution of biotinylated horse anti-mouse IgG(H+L) (Vector Laboratories) for 30 minutes, 2 μg/ml streptavidin (ICN, Aurora, Ohio) for 30 minutes, 3.5 μg/ml biotinylated peroxidase (ICN) for thirty minutes. PBS supplemented with 1% horse serum was used as a diluent throughout the assay, and plates were washed extensively in tap water between treatments. For PRNT, endpoint serum dilutions providing 50% reduction in the number of foci over control wells that contained no immune serum were counted as positive.

EXAMPLE 1

Preparation of Infectious Clone of West Nile Virus

This example is set forth in Yamshchikov, An Infectious Clone of the West Nile Flavivirus, 1: Virology. 2001 Mar. 15; 281(2):294-304, which is incorporated by reference in its entirety.

Cell Culture and Viruses

BHK-21 (Bredenbeek et al., 1993) and Vero (ATCC CRL-1586) cells were maintained at 37° C. in humidified atmosphere containing 5% $CO_2$ in Dulbecco's modified Eagle medium ("DMEM") supplemented with 5% fetal calf serum ("FCS", Hyclone) and 13 antibiotic±antimycotic mixture (GIBCO-BRL). Aedes albopictus clone C6/36 (ATCC CRL-1660) cells were maintained at 28° C. in the same media supplemented with 10% FCS. The WN strain used in this study was recovered after electroporation of BHK cells with archival RNA isolated from virus WN956D1173B, which had been triply plaque-purified in Vero cells and grown in BHK cells (Wengler and Gross, 1978). The previous passage history of this virus is unknown. Viruses recovered from infectious clones (see below) were prepared in BHK cells. All procedures involving infectious material were performed under Biological Safety Level 3 containment.

Plasmid Construction

DNA was manipulated using standard procedures (Sambrook et al., 1989) with commercially available enzymes. Throughout the study, NIH Guidelines for Research involving Recombinant DNA Molecules were followed. E. coli strain HB11 (F⁻ D(gpt-proA)62 leuB6 supE44 ara-14 galK2 lacY1 D(mcrC-nrr) rpsL20(Str') xyl-5 mtl-1 recA13) was used for cloning and maintenance of recombinant constructs. Sequencing of PCR and cDNA fragments and plasmids was done using an ABI 310 Genetic Analyzer and an ABI Prizm 377 DNA Sequencer (PE Applied Biosystems, Foster City, Calif.) using kits supplied by the manufacturer.

Plasmids pGEM-K and p32E11 containing two overlapping cDNA fragments spanning pos. 1±9550 nt of the WN genome have been described (Farber, 1990). Using overlapping PCR, the SP6 promoter was reengineered to the beginning of WN sequence and the ClaI±Bgl-II SP6-WN59 conjunct fragment was used to replace the WN 59-end fragment in pGEM-K resulting in pSP6WN59. PCR-mediated deletion of a 2150-bp WN genome fragment (pos. 162±2312) from this plasmid resulted in a SP6WNrep59 cassette, which was excised by ClaI and Asp718, and subcloned together with a 4136-bp Asp718±XbaI fragment from p32E11 between ClaI and XbaI (created in place of SalI) in pBR322 to produce a $SP6WNrep(NS5_{544})$ cassette. The remaining 1562-bp fragment encoding the carboxy-terminal part of NS5 and WN 39-UTR was recovered by RT-PCR of total RNA isolated from cells infected with WN 956 virus and was joined to the rest of the genome by overlapping PCR with simultaneous introduction of a unique Xba site at the end of the WN 39-UTR and mutation of the XbaI site at pos. 9460. To restore genes of the structural proteins, a BglII±NsiI fragment (pos. 89±3509) from $T7WN(NS3_{243})$ (Yamshchikov and Compans, 1995) was transferred into pSP6WNrep/Xba resulting in the final WN infectious clone construct designated pSP6WN/Xba.

EXAMPLE 2

Isolation of WN 1415, a Molecular Clone of the 956D117B3 Virus

Isolate WN1415 used in this example was recovered after transfection of synthetic RNA prepared from the pSP6WN/Xba infectious clone (Yamshchikov et al., 2001) into BHK cells and was used at passage 2 in Vero cells.

For genetic characterization, total RNA was isolated from Vero cells infected with WN1415 at passage 2 after transfection. Direct sequencing of gel-purified cDNA fragments prepared from this RNA has revealed two silent substitutions in positions 4566 (C) and 8355 (U) of the WN1415 genome as compared to the reported nucleotide sequence of 956D117B3 (GenBank #M12294, SEQ ID NO. 1, which is incorporated by reference). No other differences were identified. The above substitutions, which are present in the infectious clone plasmid pWN14115 as well, likely constitute cDNA variants selected during cloning.

The nucleotide sequence of the parent 956D117B3 isolate at Vero passage 2 after its rescue from archival RNA was verified. Consensus sequencing performed without intermediate subcloning of cDNA produced a sequence identical to that reported earlier (GenBank #M12294), but also revealed several heterogeneous loci containing minor peaks, which indicated the presence of quasispecies in the viral population. In contrast, these heterogeneous loci were not found in the consensus sequence of the WN1415 clonal isolate characterized at the same passage level after recovery from RNA, thus indicating a homogeneous viral population. The stablization of the genome as DNA not only will reduce the accumulation of mutations in the viral genome as seed lots are produced to replace the previous one but will also provide a much more homogeneous population in terms of nucleotide sequence.

EXAMPLE 3

Sequence Analysis of Parent B956 and its Descendants

This example investigated the extent of changes accumulated in the 956B117D3 genome over its passage history. In this example, the original B956 strain at mouse brain passage 2 was obtained from Dr. R. Shope (Galveston, Tex.). The B956 virus was passaged once in C6/36 cells and total RNA isolated from virus-infected cells was used for preparation of purified cDNA fragments.

Consensus sequencing (Pugachev et al., 2002) was done after reverse transcriptase polymerase chain reaction ("RT-PCR") amplification of eight overlapping cDNA fragments spanning the entire genome of WN1415, 956D117B3 or B956 viruses using taq polymerase (Novagen). The gel-purified fragments were sequenced without intermediate subcloning steps using the ABI310 Genetic Analyzer (ABI, Foster City, Calif.). A set of sequencing primers was designed to provide overlapping sequence segments covering the entire genome in both directions based on GenBank #M12294. Contiguous sequences were assembled with AutoAssembler 2.0 software (ABI) and downstream sequence analysis was done with the Vector NTI Advance suite (InforMax, Bethesda, Md.). Folding of 3'NTR segment of genomic RNA was done with the MFOLD program available on-line (Zuker, 2003). Sequence of the prototype B956 strain is deposited in the GenBank under accession #AY532665.

The nucleotide sequence of the entire B956 genome was determined without intermediate subcloning of cDNA fragments. Comparison of the B956 sequence with the reported sequence #M12294 of the 956D117B3 isolate revealed 37 point mutations, resulting in 18 amino acid changes spread over the entire genome. The results are summarized in Table 1 below:

TABLE 1

Summary of sequence differences between B956 and 956D117B3

| Position[a] | Gene | B956p2 | 956D117B3 | Change |
|---|---|---|---|---|
| 65 | 5'-UTR | U | C | — |
| 327 | C | GCG | GCA | — |
| 540 | prM | AUC | AUU | — |
| 975 | E | UGC | UGU | — |
| 1063 | E | CUA | AUA | Leu→Ile |
| 1548 | E | ACU | ACC | — |
| 1577 | E | GCG | GAG | Ala→Glu |
| 1819 | E | AGG | CGG | — |
| 3051 | NS1 | CUG | CUA | — |
| 3332 | NS1 | GGA | GAA | Gly→Glu |
| 3553 | NS2A | CUG | AUG | Leu→Met |
| 3609 | NS2A | AUU | AUC | — |
| 4328 | NS2B | GUG | GCG | Val→Ala |
| 4437 | NS2B | GUU | GUG | — |
| 4566 | NS2B | AUU | AUC | — |
| 5793 | NS3 | UGC | UGU | — |
| 5805 | NS3 | GAC | GAU | — |
| 6509 | NS4A | GGG | GUG | Gly→Val |
| 6620 | NS4A | GCU | GUU | Ala→Val |
| 6681 | NS4A | AAA | AAG | — |
| 6709 | NS4A | AUA | GUA | Ile→Val |
| 6846 | NS4A | GAC | GAU | — |
| 6943 | NS4B | AGC | GGC | Ser→Gly |
| 6954 | NS4B | UUA | UUG | — |
| 6962 | NS4B | AAG | AGG | Lys→Arg |
| 7205 | NS4B | GCC | GUC | Ala→Val |
| 7218 | NS4B | GGC | GGU | — |
| 8290 | NS5 | GUA | AUA | Val→Ile |
| 10391 | 3'-UTR | 76 nt insert | — | — |
| 10399 | 3'-UTR | C | U | — |
| 10763 | 3'-UTR | U | A | — |
| 10929 | 3'-UTR | U | C | — |
| 10948 | 3'-UTR | G | U | — |

[a]Coordinates according to the 956D117B3 sequence (GenBank #M12294)

About 33% of these amino acid changes accumulated in NS4B, followed by NS4A, with only three found in the structural protein region, suggesting that most of the changes are associated with intracellular replication, presumably with a little or no effect on the virion properties. The most prominent is a 76 nucleotide deletion in the 3'-UTR beginning after position 10391 in the B956 genome, i.e., immediately downstream from the stop codon terminating the WN open reading frame. Two nucleotide changes were also found in the 3'-terminal stem-and-loop structure, which is conserved in flaviviruses and is important for RNA replication (Proutski et al., 1999). When the 3'-terminal 110 nucleotides of either sequence were folded using MFOLD (Zuker, 2003), both these changes were found in unpaired bulges of the otherwise completely conserved structure (results not shown) and thus probably do not play important roles.

Since the majority of amino acid substitutions were found in nonstructural proteins and in the 3'-untranslated region, this suggests changes at the intracellular stage of viral replication. However, the non-conservative change Ala→Glu at pos. E204 might also contribute to attenuation (see Example 6). This position is located to the loop between strands f and g in the dimerization domain (Rey et al., 1995), and both more virulent B956 and NY99, as well as all JE viruses sequenced to date contain an uncharged amino acid at this position. On the other hand, attenuation does not always result in accumulation of mutations in the E protein (Kinney et al., 1997), and several non-conservative changes found in NS1, NS4B and NS5, as well as 76 nt deletion in 3'-NTR may contribute to attenuation at the level of RNA replication or other stages of the virus infectious cycle (see Example 5).

EXAMPLE 4

Phenotypic Differences Between Parent B956, Isolate 956D117B3 and Viral Molecular Clone WN1415

A. In Vitro Experiments.

In this example, the cytopathic properties of the West Nile prototype strain B956 and the clonal isolate WN1415 was first investigated. BHK (top panel of FIG. 1) or Vero (lower panel of FIG. 1) monolayers were infected with 10-fold dilutions of corresponding viruses and incubated under 1% methylcellulose overlays for 4-5 days. Cells fixed with 1% HCHO were stained with Coumassie G250, washed, dried and photographed in visible light (left panels for each virus)). Coumassie stain was removed with ethanol washes, and monolayers were rehydrated in 50% alcohol followed by PBS. Virus foci were immunostained as described in below and photographed in visible light (right panels for each virus).

Figure 1:
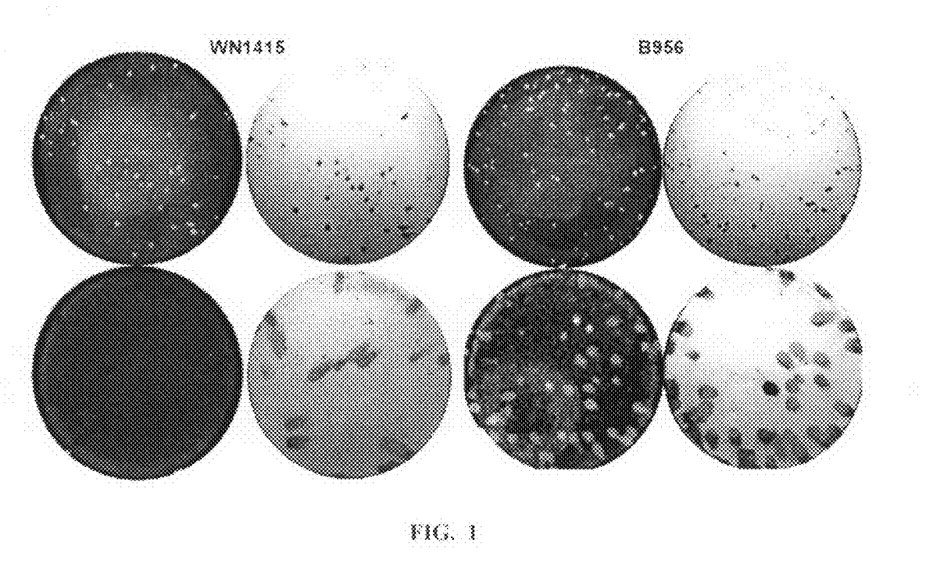

956D117B3 and WN1415 display a substantially decreased cytopathicity as compared to the B956 strain. In contrast to the latter, as shown in FIG. 1 both do not form distinguishable foci of cytopathology (plaques) in Vero cells (WN1415 and B956). However, as shown in FIG. 1, foci of virus multiplication are easily detectable by immunostaining with the DAB-peroxidase procedure. Despite the low cytopathicity, both WN1415 and 956D117B3 grow in Vero cells to high titers, which in optimal conditions may reach about $10^8$-$10^9$ pfu/ml. The more cytopathic B956 strain produced titers in the range of about $10^7$ pfu/ml. There was no difference between viruses in plaque formation in BHK cells.

B. In Vivo Experiments.

Swiss Webster (ICR) or NIH Swiss outbred mice were purchased from Hilltop Lab Animals Inc. (Scottsdale, Pa.) and Harlan Spargue Dawley (Indianapolis, Ind.), respectively, maintained in a BL3 facility according to the NIH guidelines, and used in IACUC-approved protocols. Mice were anesthetized with metofane (Mallinckrodt Veterinary, Mundelein, Ill.) and infected into the Tibialis anterior muscle (i.m.) or intracerebrally (i.c.) with virus diluted in PBS plus 0.2% of normal mouse serum. The $LD_{50}$ (50% lethal dose) was calculated by the Reed and Muench method (Burleson et al., 1992). Mice were observed daily for the development of encephalitis and mortality. Moribund mice were euthanased.

In one aspect, peripheral virulence was assessed in 4-week-old outbred mice, which were infected i.m. with 10-fold virus dilutions. Thirty-six mice were examined with the control group of 6 mice receiving the diluent only. As shown in Table 2, 100% mortality could not be achieved even at highest i.m. dose used. The $LD_{50}$ for WN1415 by this route was found to be $6.6 \times 10^6$ pfu. The 956D117B3 virus, which was not molecularly cloned, showed a slightly higher virulence with $LD_{50}$ of $1.1 \times 10^6$ pfu for i.m. inoculation (Table 2).

TABLE 2

Virulence of WN1415 and 956D117B3 in NIH Swiss mice by the i.m. route

| WN1415[a] | D/T[b] | %[b] | 956D117B3[a] | D/T[b] | %[b] |
|---|---|---|---|---|---|
| 4.9E+07 | 5/6 | 83 | 4.0E+07 | 4/6 | 66 |
| 4.9E+06 | 2/6 | 33 | 4.0E+06 | 4/6 | 66 |
| 4.9E+05 | 1/6 | 17 | 4.0E+05 | 3/6 | 50 |
| 4.9E+04 | 1/6 | 17 | 4.0E+04 | 1/6 | 17 |
| 4.9E+03 | 0/6 | 0 | 4.0E+03 | 0/6 | 0 |
| 4.9E+02 | 0/6 | 0 | 4.0E+02 | 0/6 | 0 |
| 0 | 0/6 | 0 | 0 | 0/6 | 0 |
| $LD_{50}$ = 6.62E+06 | | | $LD_{50}$ = 1.13E+06 | | |

[a]pfu per mouse;
[b]mortality after two weeks (D/T—dead/total)

By the i.c route, WN1415 showed $LD_{50}$ of 158 pfu for adult 7-weeks old mice, but the uncloned 956D117B3 isolate appeared about 10-fold more neurovirulent with $LD_{50}$ Of only 13.5 pfu (Table 3).

TABLE 3

Infectivity of WN1415 and 956D117B3 in NIH Swiss mice by the i.c. route

| WN1415[a] | D/T[b] | %[b] | 956D117B[a] | D/T[b] | %[b] |
|---|---|---|---|---|---|
| — | — | — | 5.2E+03 | 3/3 | 100 |
| 5E+02 | 3/3 | 100 | 5.2E+02 | 6/6 | 100 |
| 5E+01 | 0/3 | 0 | 5.2E+01 | 5/6 | 83 |
| 5E+00 | 0/3 | 0 | 5.2E+00 | 1/3 | 33 |
| 5E−01 | 0/3 | 0 | — | — | — |
| $LD_{50}$ = 1.58E+02 | | | $LD_{50}$ = 1.35E+01 | | |

[a]pfu per mouse;
[b]mortality after two weeks (D/T—dead/total)

The observed differences may have resulted from the presence of quasispecies with a higher virulence in the uncloned 956D117B3 population. There was no heterogeneity in size of 956D 117B3 multiplication foci both in Vero and in BHK cells, which is consistent with the fact that the RNA from which the virus was rescued had been extracted from a triple plaque purified virus (Wengler and Beato, 1979). As mentioned above, consensus sequencing did reveal several heterogeneous loci in the 956D117B3 genome indicative of the presence of quasispecies, although a detailed functional analysis of these was not performed.

The parent B956 strain was found to be about 50 times more virulent than WN1415 upon i.m. infection, with $LD_{50}$ of $1.24 \times 10^5$ pfu (Table 4). In a sharp contrast to the B956 group, $LD_{50}$ for NY99 was found to be only 19 pfu (Table 4), which agrees with earlier reports (Beasley et al., 2002) documenting the high pathogenicity of this strain. Similar results were obtained after i.p. inoculation of NY99 as well (data not shown).

TABLE 4

Virulence of B956 and NY99 in NIH Swiss mice by the i.m. route

| B956[a] | D/T[b] | %[b] | NY99[a] | D/T[b] | %[b] |
|---|---|---|---|---|---|
| 2.2E+06 | 5/6 | 83 | — | — | — |
| 2.2E+05 | 4/6 | 66 | 1E+05 | 6/6 | 100 |
| 2.2E+04 | 1/6 | 17 | 1E+04 | 6/6 | 100 |
| 2.2E+03 | 0/6 | 0 | 1E+03 | 5/6 | 83 |
| 2.2E+02 | 0/6 | 0 | 1E+02 | 5/6 | 83 |
| 2.2E+01 | 0/6 | 0 | 1E+01 | 3/6 | 50 |
| 0 | 0/6 | 0 | 0 | 0/6 | 0 |
| $LD_{50}$ = 1.24E+05 | | | $LD_{50}$ = 1.93E+01 | | |

[a]pfu per mouse;
[b]mortality after two weeks (D/T—dead/total)

Infection with lethal doses of NY99 uniformly resulted in rapidly progressing encephalitis accompanied by para- or even quadriplegia and resolved by death often in less than 12 hours after onset of neurological symptoms. In contrast, infection with lethal doses of WN1415 resolved in 2-3 days and was characterized by immobility, anorexia and a substantial weight loss, but paralytic symptoms were uncommon. Neurological symptoms such as paralysis more often were observed with 956D117B3, thus corroborating its heterogeneous nature. The provided evidence indicates that clonal purification of 956D117B3 using the infectious clone technology has yielded the homogeneous viral clone characterized by a lower residual virulence in the mouse model.

EXAMPLE 5

Virus-Specific Humoral Response

In this example, the humoral response of 956D117B3 was investagatedFor both 956D117B3 and its WN1415 clonal isolate, the identity with the NY99 strain is only 79.4% at the nucleotide level, thus confirming assignment of two strains to separate lineages (Berthet et al., 1997; Lanciotti et al., 1999). The overall identity of both viruses at the level of the amino acid sequence is 93.8%, which is unevenly distributed among individual proteins (Table 5).

TABLE 5

The identity of WN strains NY99a and WN1415b at the protein level

| | C | prM(M) | E | NS1 | NS2A | NS2B | NS3 | NS4A | NS4B | NS5 |
|---|---|---|---|---|---|---|---|---|---|---|
| % identity | 97 | 96(96) | 94 | 92 | 89 | 98 | 96 | 93 | 91 | 95 |

[a]GenBank #AF196835
[b]GenBank #M12294

At the 94% sequence identity between envelope proteins of NY99 and WN1415, induction of cross-reactive antibodies and a certain level of cross-protective immunity could be expected. To evaluate that, titers of NY99 cross-reacting antibodies and the neutralizing activity of the immune sera against the NY99 strain were determined in mice, which survived immunization with 956D117B3 or WN1415. For challenge experiments (see Example 7), the anesthetized mice were inoculated i.m. with 10 i.m. $LD_{50}$ (unless specified otherwise) of NY99 virus. The 385-99 isolate of the NY99 strain (at Vero passage 1) was generously provided by Dr. Tesh (Galveston, Tex.). The NY99 virus was grown once in C6/36 cells and were used after an additional passage in Vero cells. Mice were observed daily for the development of encephalitis and mortality. Moribund mice were euthanased.

For ELISA, the coating antigen was prepared from 956D117B3 or NY99 viruses pelleted through 20% sucrose cushion from media of infected Vero cells. The three-hour centrifugation at 25,000 rpm was done using a Beckman SW28 rotor. The pellet was resuspended in 50 mM triethanolamine-HCl pH 8.5, 100 mM NaCl, and 0.5% Triton X-100 to extract viral envelope subunit antigen (Heinz et al., 1981). Clarified supernatant (1000×g, 15 minutes, 4° C.) was stored at –80° C. and was used at 1:500 dilution in PBS. Serial 2-fold dilutions of immune sera were tested in duplicate using a goat anti-mouse IgG(H+L) peroxidase conjugate with the TMB substrate (Sigma-Aldrich, St. Louis, Mo.). Assays were read at 450 nm using PowerWave XS microplate reader equipped with KC-4 software (Bio-Tek, Winooski, Vt.). Readings of two standard deviations above the background (serum from control mice used at the same dilution) were considered positive.

Figure 2:
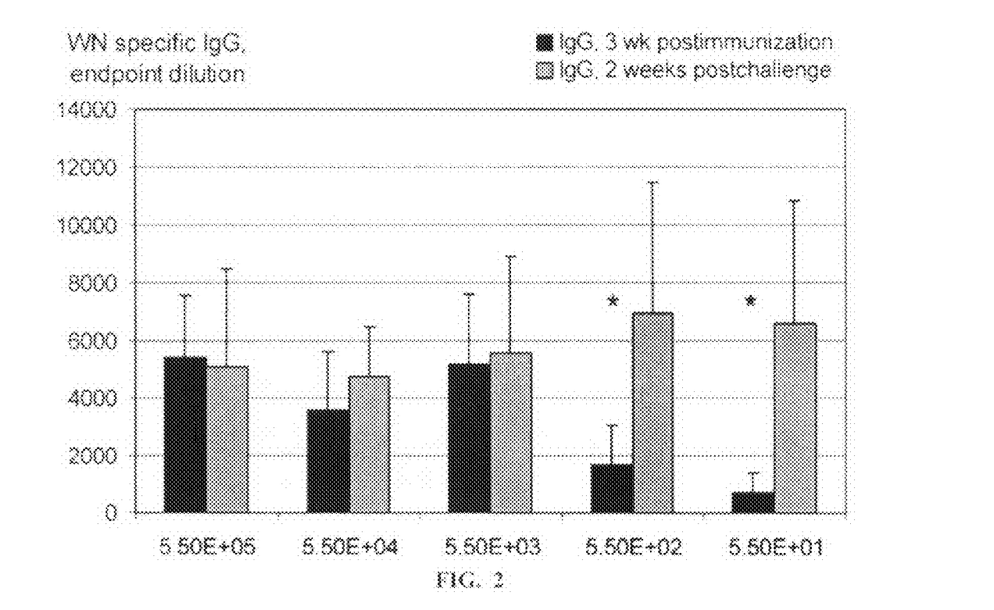

Both 956D117B3 and NY99 antigens produced very similar readings with the tested sera in ELISAs specific for antiviral IgG. The levels of WN-specific IgG at 3 weeks post immunization with WN1415 and at two weeks post challenge with NY99 are shown in FIG. 2 as endpoint dilutions of averaged sera yielding positive readouts with the NY99 antigen. Higher virus doses resulted in earlier appearance of WN-specific antibodies (data not shown), and all survived mice developed detectable antiviral humoral immunity by three weeks post infection, in serum dilutions ranging from 400 to 6400 depending on virus dosage. By this time, mice in all dosage groups have already demonstrated substantial titers of neutralizing antibodies against the NY99 strain (Table 6). Thus, combination of virus IgG-specific ELISA and data on neutralizing antibody titers confirmed the high antigenic similarity of both viruses, and suggest that efficient protection against NY99 infection may be expected after WN1415 immunization.

TABLE 6

Development of NY99 neutralizing immunity a after WN1415 immunization[b]

| Mouse No. | WN1415 dose, pfu/mouse | | | | |
|---|---|---|---|---|---|
| | 5.5E+05 | 5.5E+04 | 5.5E+03 | 5.5E+02 | 5.5E+01 |
| 1 | 160 | ND | 320 | 160 | ND |
| 2 | 80 | 320 | 80 | 80 | ND |
| 3 | ND | 160 | 160 | 40 | 160 |
| 4 | 160 | 80 | ND | ND | 160 |
| 5 | 160 | ND | ND | 80 | ND |
| 6 | 40 | 320 | 640 | 160 | 40 |

[a]NY99 neutralizing titer at 3 weeks post immunization
[b]ND - mice died after either the primary immunization, or the challenge, or for unrelated reasons

EXAMPLE 6

Immunization with WN1415 Confers Strong Protection Against NY99 Challenge

In this example, six groups of 3-weeks-old Swiss Webster outbred mice (6 mice per group, 36 mice total) were injected i.m. with clonal WN1415 isolate recovered after transfection of BHK cells. Titer of the virus stock was $5.5 \times 10^6$ pfu/ml. The amount of virus per mice in 100 μl varied as set forth in Table 7. Injections were done with the virus diluted in PBS with 0.1% of mouse serum. Dilutions were done in a volume of 1 ml (0.1 ml of upper dilution+0.9 ml of 1% mouse serum in PBS).

Three weeks after inoculation with various doses of WN1415 (as shown in Table 7) all survived mice were challenged i.m. with 10 $LD_{50}$ of NY99 strain. Eighty five percent of mice, which had survived the WN1415 infection, have survived the lethal challenge with NY99, whereas none survived in the control group (Table 7). Although 100% protection was observed only in mice that received the two highest doses of WN1415, 67% of mice immunized with only 55 pfu of WN1415 where able to fend off the infection. During the two-week observation period after the challenge, neither of mice that survived the challenge have displayed any signs of disease, such as immobility, ruffled fur or anorexia, while all mice in the control group have succumbed to paralytic encephalitis between 8 to 11 days post challenge. In the three highest WN1415 dosage groups mice did not display statistically significant changes in the titer of virus specific antibodies after the challenge (FIG. 2), indicating that infection with NY99 was very limited or was completely suppressed. In contrast, mice that survived the challenge in the two lowest WN1415 dosage groups did show a significant increase in average antibody titers by two weeks after challenge (FIG. 2, p values 0.026 and 0.022 for 5.5E+02 and 5.5E+01 pfu correspondingly), indicating that infection with NY99 virus was not prevented. However, we have not observed any disease symptoms in these mice. Whether immunization with lower doses of WN1415 has induced a potent cell-mediated immunity, which has helped to curb and eventually eliminate infection, requires a more detailed investigation.

TABLE 7

Survival of immunized mice after NY99 challenge

| WN1415[a] | S1/S2[b] | %[b] | 956D117B3[a] | S1/S2[b] | %[b] |
|---|---|---|---|---|---|
| 5.5E+05 | 5/5 | 100 | 1E+06 | 2/2 | 100 |
| 5.5E+04 | 4/4 | 100 | 1E+05 | 4/4 | 100 |
| 5.5E+03 | 5/4 | 80 | 1E+04 | 4/4 | 100 |
| 5.5E+02 | 6/5 | 83 | 1E+03 | 5/5 | 100 |
| 5.5E+01 | 6/4 | 67 | 1E+02 | 5/5 | 100 |
| 0 | 6/0 | 0 | 0 | 6/0 | 0 |
| NY99 dose: 10 $LD_{50}$, i.m. | | | NY99 dose: 100 $LD_{50}$, i.p. | | |

[a]primary immunization, pfu/mouse
[b]S1-survived after primary immunization; S2-survivied the challenge Inoculation with the more virulent 956D117B3 isolate resulted in a higher mortality rate (Table 2), but has also conferred a stronger protection upon survived mice since 100% survival was observed in all dosage groups after i.p. challenge with 10-fold higher doses of NY99 (100 i.p. $LD_{50}$; Table 7). While older mice have been used in this experiment, the age did not appear to contribute to the observed increase in survival since the challenge with NY99 still resulted in 100% mortality in the control group of mice (Table 7). These data suggest that more virulent quasispecies present in the 956D117B3 population may have substantially increased the potency of the preparation. On the other hand, while less virulent WN1415 has obviously lost some potency, it was still able to induce a sufficient protection in immunized animals.

Until the present invention, it was not clear whether a lineage 2 virus is capable to induce a strong protective immunity against the highly pathogenic lineage 1 NY99 strain and will not result in an opposite effect of the immune enhancement, which had been described for homologous and heterologous viruses of the JE serocomplex and WN in particular both in mice (Fagbami et al., 1987; Gollins and Porterfield, 1985; Lobigs, Pavy, and Hall, 2003) and observed with sera of naturally immunized human population (Fagbami et al., 1988). In this example, immunization with attenuated derivatives of B956, the 956D117B3 isolate and its clonal variant WN1415, induced potent immune responses capable of protecting against infection with the highly virulent NY99 strain. Immunization with doses in the range of $5.5\times10^3$ to $5.5\times10^5$ pfu of WN1415 (roughly equivalent to 35-3,500 mouse i.c. $LD_{50}$) induced a substantial level of NY99 neutralizing antibodies detectable as early as three weeks post immunization and the resulting immunity protected almost all immunized animals from infection with NY99. Although a direct comparison cannot be made, a single human dose of YF17D vaccine is required to contain at least 1,000 mouse i.c. $LD_{50}$ (WHO, 1998), but in fact most preparations contain between 5,000-10,000 $LD_{50}$ per dose (Barrett, 1997). The majority of mice immunized with doses 55-550 pfu (0.35-3.5 mouse i.c. $LD_{50}$) also withstood the challenge, even though the infection was not prevented as indicated by the several fold increase in post-challenge IgG titers.

Since cell-mediated immunity plays a major role in clearance of viral infection (Engle and Diamond, 2003; Murphy and Chanock, 1996), one may suggest that immunization with lower doses of WN1415 induced a cell-mediated response strong enough to terminate developing infection. Future experiments on the status of cell-mediated immunity after immunization with WN1415 are currently being performed.

EXAMPLE 7

Design of Flavivirus Infectious DNA

This example uses an intron-based stabilization approach to design the routinely stable flavivirus infectious DNA. Internal destabilizing elements, such as bacterial promoter-like sequences driving expression of genome segments encoding toxic peptides, occurring throughout the flavivirus genome are major destabilizing factors of flavivirus infectious clone constructs significantly complicating propagation of corresponding plasmids in bacterial hosts. Introns inserted in upstream from these destabilizing sequences eliminate expression of toxic peptides in bacterial hosts and result in complete stabilization of corresponding plasmid constructs. Upon transfection into mammalian cells the introns are precisely spliced out by the nuclear transcription machinery resulting in complete restoration of viral open reading frame which direct synthesis of a normal set of virus specific proteins. An intron-based stabilization approach (Johansen, 1996) has been implemented in the design of routinely stable JE virus infectious DNA (Yamshchikov, Mishin, and Cominelli, 2001), but never in a West Nile construct.

Figure 3:
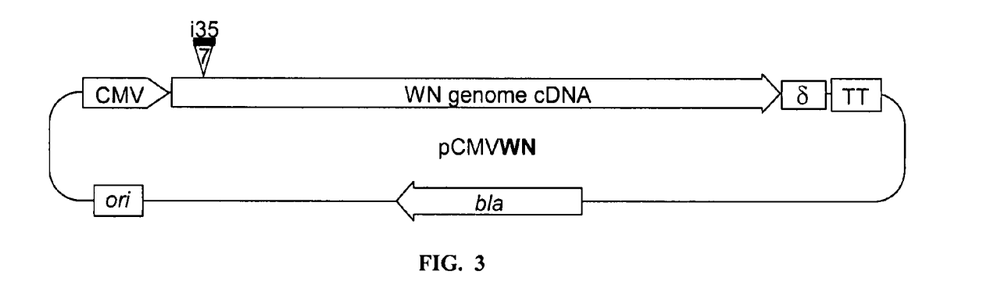

To test the applicability of this approach for stabilization of infectious clones of other flaviviruses, the design infectious DNA of the WN clone (Yamshchikov et al., 2001) was investigated. Specifically, plasmid pSP6WN/Xba (Yamshchikov et al. 2001) was used in construction of WN infectious DNA, in which ClaI -MluI fragment was replaced with a fragment containing CMV promoter and a chimeric intron from pCI-neo (Promega) was inserted at pos. 357 of WN genome (FIG. 3).

Plasmid DNAs for mice inoculation were purified using QIAGEN EndoFree Plasmid Maxi kit (Qiagen, Valencia, Calif.); the residual endotoxin content was within limits specified by the manufacturer.

In contrast to similarly arranged JE infectious DNA, insertion of only one intron at pos. 357 of the viral genome, i.e. upstream from the prM signal sequence occurring as the first stretch of hydrophobic amino acids in the WN polyprotein, was adequate to stabilize the construct placed downstream from the CMV promoter. The internal destabilizing element, presumably a bacterial promoter-like sequence located in the E gene, which is a major destabilizing factor for an infectious clone of JE virus (Yamshchikov, Mishin, and Cominelli, 2001), was not found in WN956D117B3, genome thus obviating the requirement for a second intron insertion upstream from the NS1 gene. Resulted plasmid pCMVWN (FIG. 3) had the same stability and growth characteristics in *E. Coli* HB101 as the parent plasmid pSP6WN/Xba (data not shown). This evidence implies that insertion of an intron upstream from the prM signal sequence may be universally required in the design of stable flavivirus infectious DNA, while additional introns may be required depending on virus-specific presence of destabilizing elements.

It will be further appreciated the present invention now also provides the possibility of generating a modified infectious clone via the further application of recombinant DNA technology. Such modifications may be single or multiple mutations, substitutions, deletions or insertions or combinations thereof that can be achieved via any recombinant DNA technology method known in the art. The present invention thus provides modified RNA viruses that can be used to investigate RNA viruses and to prepare vaccines.

EXAMPLE 7

Infectivity of Flavivirus DNA Constructs in Mice

In this example, the infectivity of the flavivirus plasmid infectious DNA construct of the present invention was investigated and successfully demonstrated using different administration routes.

a. DNA Inoculation Overview

Swiss Webster (ICR) mice were purchased Tom Hilltop Lab Animals Inc. (Scottsdale, Pa.), maintained in a BL3 facility according to the NIH guidelines and used in IACUC-approved protocols. Mice were injected into the Tibialis anterior muscle (im) with 50 µl or, after anesthesia with metofane (Mallinckrodt Veterinary, Mundelein, Ill.), intracerebrally (ic) with 20 µl of infectious DNA solution in PBS using a 28G needle. For intradermal (id) administration of DNA, cartridges for Helios Gene Gun system (BioRad) containing 0.25 mg of 1.6 µm golden particles coated with 0.1-10 µg of plasmid DNA were prepared according to the manufacturer and applied to shaved disinfected abdominal skin at helium discharge pressure of 400 psi. Inoculation by ic, im, and intradermally all showed evidence of infectious viral infection.

For example, since intracerebral inoculation of RNA was shown to be a very sensitive method of virus rescue from flavivirus infectious clones (Gritsun and Gould, 1995), this example used this route of inoculation to determine if DNA infectious in cell culture remains infectious in animals.

Viruses encoded by constructs were isolated from brains of all fatal cases confirming that mice indeed succumbed to infection. Virus-specific antibodies were detected down to the lowest doses of DNA used, indicating that mice were exposed to viral antigens and likely were able to fend off the infection with low amounts of virus produced from infectious DNA.

The effects of intradermal administration of infectious DNA using the biolistic (Gene Gun) method were investigated. Numerous evidence from DNA immunization studies indicate that intradermal administration of DNA with Gene Gun appears effective with 100 ng of DNA or less (Fynan et al., 1993; Pertmer et al., 1995), as compared to needle immunization generally used in about 10 to about 100 µg dose range. For synthetic infectious RNA, 1 ng was found to be effective for establishment of infection as indicated by development of anti-viral immunity (Mandl et al. 1998).

Biolistic administration of infectious DNA to 6 weeks old mice resulted in outcome resembling that observed upon i.m. DNA inoculation. The mortality rate did not coincide with maximum dosage and was maximal only at a certain optimal infectious DNA dosage, which appeared about 10-fold less than for i.m. inoculation.

The above experiments indicated that a plasmid carrying the full flavivirus genome controlled by eukaryotic transcription elements is infectious in mice via different inoculation routes, with biolistic intradermal inoculation being the most efficient one.

EXAMPLE 8

Immunization with Infectious DNA

In this example, the protective immune response of the infectious DNA construct was investigated and successfully demonstrated. Six groups of 3-weeks-old Swiss Webster outbred mice (6 mice per group, 36 mice total) were injected in Tibialis interior muscle with infectious DNA pCMVWN. The amount of plasmid per mouse in each group was as follows:

1. 10 µg (50 µg, 200 µg/ml in PBS)
2. 1 µg+9 µg carrier
3. 100 ng+9.9 µg carrier
4. 10 ng+9.99 µg carrier
5. 1 ng+9.999 µg carrier
6. 0 ng+10 µg carrier Needle injection was done with endotoxin free plasmid dissolved or diluted accordingly in PBS+200 µg/ml of vector plasmid in a total volume of 50 µl. After an observation period of two weeks, survived mice were challenged i.m. with 500 pfu of NY99 and observed for another two week period. The results are set forth below:

| Inoculum | Survived Total After Inoculation with Infectious DNA | Survived/Total (%) After Challenged with NY99 |
| --- | --- | --- |
| 10 µg | 6/6 | 4/6 (66*) |
| 1 µg | 6/6 | 5/6 (83) |
| 100 ng | 6/6 | 3/6 (50) |
| 10 ng | 5/6 | 0/5 (0) |
| 1 ng | 6/6 | 0/6 (0) |
| 0 ng | 6/6 | 0/6 |

*Two mice were inadvertently killed during test bleeding

All publications mentioned herein are incorporated herein by reference to describe the methods and/or materials in connection with which the publications are cited.

Aihara, S., Rao, C. M., Yu, Y. X., Lee, T., Watanabe, K., Komiya, T., Sumiyoshi, H., Hashimoto, H., and Nomoto, A. (1991). Identification of mutations that occurred on the genome of Japanese encephalitis virus during the attenuation process. *Virus Genes* 5, 95-109.

Anonymous. (2003). Study: West Nile virus cost equine industries in Colorado, Nebraska millions in 2002. *J Am Vet Med Assoc* 222, 1669, 1672.

Arroyo, J., Guirakhoo, F., Fenner, S., Zhang, Z. X., Monath, T. P., and Chambers, T. J. (2001a). Molecular basis for attenuation of neurovirulence of a yellow fever Virus/Japanese encephalitis virus chimera vaccine (ChimeriVax-JE). *J Virol* 75, 934-42.

Arroyo, J., Miller, C. A., Catalan, J., and Monath, T. P. (2001b). Yellow fever vector live-virus vaccines: West Nile virus vaccine development. *Trends Mol Med* 7(8), 350-4.

Barrett, A. D. (1997). Yellow fever vaccines. *Biologicals* 25(1), 17-25.

Beasley, D. W., and Barrett, A. D. (2002). Identification of neutralizing epitopes within structural domain III of the West Nile virus envelope protein. *J Virol* 76(24), 13097-100.

Beasley, D. W., Li, L., Suderman, M. T., and Barrett, A. D. (2002). Mouse neuroinvasive phenotype of West Nile virus strains varies depending upon virus genotype. *Virology* 296 (1), 17-23.

Berthet, F. X., Zeller, H. G., Drouet, M. T., Rauzier, J., Digoutte, J. P., and Deubel, V. (1997). Extensive nucleotide changes and deletions within the envelope glycoprotein gene of Euro-African West Nile viruses. *J Gen Virol* 78(Pt 9), 2293-7.

Bredenbeek, P. J., Frolov, I., Rice, C. M., and Schlesinger, S. (1993). Sindbis virus expression vectors: packaging of RNA replicons by using defective helper RNAs. *Journal of Virology* 67(11), 6439-46.

Burleson, F. G., Chambers, T. M., and Wiedbrauk, D. L. (1992). "Virology: A Laboratory Manual." Academic Press Inc., San Diego, New York, Boston, London, Sydney, Tokyo, Toronto.

Castle, E., Leidner, U., Nowak, T., and Wengler, G. (1986). Primary structure of the West Nile flavivirus genome region coding for all nonstructural proteins. *Virology* 149(1), 10-26.

Castle, E., Nowak, T., Leidner, U., and Wengler, G. (1985). Sequence analysis of the viral core protein and the membrane-associated proteins V1 and NV2 of the flavivirus West Nile virus and of the genome sequence for these proteins. *Virology* 145(2), 227-36.

Castle, E., and Wengler, G. (1987). Nucleotide sequence of the 5'-terminal untranslated part of the genome of the flavivirus West Nile virus. *Arch Virol* 92(3-4), 309-13.

CDC. (2004). West Nile Virus. 2003 Human Cases.

Co, M. D., Terajima, M., Cruz, J., Ennis, F. A., and Rothman, A. L. (2002). Human cytotoxic T lymphocyte responses to live attenuated 17D yellow fever vaccine: identification of HLA-B35-restricted CTL epitopes on nonstructural proteins NS1, NS2b, NS3, and the structural protein E. *Virology* 293 (1), 151-63.

Diamond, M. S., Shrestha, B., Mehlhop, E., Sitati, E., and Engle, M. (2003). Innate and adaptive immune responses determine protection against disseminated infection by West Nile encephalitis virus. *Viral Immunol* 16(3), 259-78.

Eckels, K. H., and Putnak, R. (2003). Formalin-inactivated whole virus and recombinant subunit flavivirus vaccines. *Adv Virus Res* 61, 395-418.

Engle, M. J., and Diamond, M. S. (2003). Antibody prophylaxis and therapy against West Nile virus infection in wild-type and immunodeficient mice. *J Virol* 77(24), 12941-9.

Fagbami, A., Halstead, S. B., Marchette, N., and Larsen, K. (1988). Heterologous flavivirus infection-enhancing antibodies in sera of Nigerians. *Am J Trop Med Hyg* 38(1), 205-7.

Fagbami, A. H., Halstead, S. B., Marchette, N.J., and Larsen, K. (1987). Cross-infection enhancement among African flaviviruses by immune mouse ascitic fluids. *Cytobios* 49(196), 49-55.

Farber, P. M. (1990). Doctoral. Justus-Liebig-Universitat Giessen, Giessen.

Gollins, S. W., and Porterfield, J. S. (1985). Flavivirus infection enhancement in macrophages: an electron microscopic study of viral cellular entry. *J Gen Virol* 66(Pt 9), 1969-82.

Hammam, H. M., Clarke, D. H., and Price, W. M. (1965). Antigenic variation of West Nile virus in relation to geography. *Am. J. Epidemiol.* 82, 40-55.

Heinz, F. X., Tuma, W., and Kunz, C. (1981). Antigenic and immunogenic properties of defined physical forms of tick-borne encephalitis virus structural proteins. *Infect Immun* 33(1), 250-7.

Kahler, S. C. (2003). APHIS: West Nile virus vaccine safe for use. *J Am Vet Med Assoc* 223(4), 416-8.

Kinney, R. M., Butrapet, S., Chang, G. J., Tsuchiya, K. R., Roehrig, J. T., Bhamarapravati, N., and Gubler, D. J. (1997). Construction of infectious cDNA clones for dengue 2 virus: strain 16681 and its attenuated vaccine derivative, strain PDK-53. *Virology* 230(2), 300-8.

Lai, C. J., and Monath, T. P. (2003). Chimeric flaviviruses: novel vaccines against dengue fever, tick-borne encephalitis, and Japanese encephalitis. *Adv Virus Res* 61, 469-509.

Lanciotti, R. S., Roehrig, J. T., Deubel, V., Smith, J., Parker, M., Steele, K., Crise, B., Volpe, K. E., Crabtree, M. B., Scherret, J. H., Hall, R. A., MacKenzie, J. S., Cropp, C. B., Panigrahy, B., Ostlund, E., Schmitt, B., Malkinson, M., Banet, C., Weissman, J., Komar, N., Savage, H. M., Stone, W., McNamara, T., and Gubler, D. J. (1999). Origin of the West Nile virus responsible for an outbreak of encephalitis in the northeastern United States. *Science* 286(5448), 2333-7.

Langevin, S. A., Arroyo, J., Monath, T. P., and Komar, N. (2003). Host-range restriction of chimeric yellow fever-West Nile vaccine in fish crows (Corvus ossifragus). *Am J Trop Med Hyg* 69(1), 78-80.

Lobigs, M., Pavy, M., and Hall, R. (2003). Cross-protective and infection-enhancing immunity in mice vaccinated against flaviviruses belonging to the Japanese encephalitis virus serocomplex. *Vaccine* 21(15), 1572-9.

Marchevsky, R. S., Mariano, J., Ferreira, V. S., Almeida, E., Cerqueira, M. J., Carvalho, R., Pissurno, J. W., da Rosa, A. P., Simoes, M. C., Santos, C. N., and et al. (1995). Phenotypic analysis of yellow fever virus derived from complementary DNA. *Am J Trop Med Hyg* 52(1), 75-80.

Monath, T. P. (1999). Yellow fever. 3rd edition ed. In "Vaccines" (S. Plotkin, and W. Orenstein, Eds.), pp. 815-879. W B Saunders Company, Philadelphia.

Monath, T. P., Arroyo, J., Levenbook, I., Zhang, Z. X., Catalan, J., Draper, K., and Guirakhoo, F. (2002). Single mutation in the flavivirus envelope protein hinge region increases neurovirulence for mice and monkeys but decreases viscerotropism for monkeys: relevance to development and safety testing of live, attenuated vaccines. *J Virol* 76(4), 1932-43.

Monath, T. P., Arroyo, J., Miller, C., and Guirakhoo, F. (2001). West Nile virus vaccine. *Curr Drug Targets Infect Disord* 1(1), 37-50.

Murgue, B., Murri, S., Triki, H., Deubel, V., and Zeller, H. G. (2001). West Nile in the Mediterranean basin: 1950-2000. *Ann N Y Acad Sci* 951, 117-26.

Murphy, B. R., and Chanock, R. M. (1996). Immunization against viral disease. 3d edition ed. In "Fields Virology" (B. N. Fields, D. M. Knipe, P. M. Howley, R. M. Chanock, J. L. Melnick, T. P. Monath, B. Roizman, and S. E. & Strauss, Eds.), Vol. 1, pp. 467-497. 2 vols. Lippincott-Raven, Philadelphia.

Ng, T., Hathaway, D., Jennings, N., Champ, D., Chiang, Y. W., and Chu, H. J. (2003). Equine vaccine for West Nile virus. *Dev Biol (Basel)* 114, 221-7.

Ni, H., and Barrett, A. D. (1996). Molecular differences between wild-type Japanese encephalitis virus strains of high and low mouse neuroinvasiveness. *J Gen Virol* 77 (Pt 7), 1449-55.

Ni, H., Chang, G. J., Xie, H., Trent, D. W., and Barrett, A. D. (1995). Molecular basis of attenuation of neurovirulence of wild-type Japanese encephalitis virus strain SA14. *J Gen Virol* 76(Pt 2), 409-13.

Nusbaum, K. E., Wright, J. C., Johnston, W. B., Allison, A. B., Hilton, C. D., Staggs, L. A., Stallknecht, D. E., and Shelnutt, J. L. (2003). Absence of humoral response in flamingos and red-tailed hawks to experimental vaccination with a killed West Nile virus vaccine. *Avian Dis* 47(3), 750-2.

Pletnev, A. G., Putnak, R., Speicher, J., Wagar, E. J., and Vaughn, D. W. (2002). West Nile virus/dengue type 4 virus chimeras that are reduced in neurovirulence and peripheral virulence without loss of immunogenicity or protective efficacy. *Proc Natl Acad Sci USA* 99(5), 3036-41.

Price, W. H., and O'Leary, W. (1967). Geographic variation in the antigenic character of West Nile virus. *American Journal of Epidemiology* 85(1), 84-86.

Proutski, V., Gritsun, T. S., Gould, E. A., and Holmes, E. C. (1999). Biological consequences of deletions within the 3'-untranslated region of flaviviruses may be due to rearrangements of RNA secondary structure. *Virus Res* 64(2), 107-23.

Pugachev, K. V., Guirakhoo, F., Trent, D. W., and Monath, T. P. (2003). Traditional and novel approaches to flavivirus vaccines. *Int J Parasitol* 33(5-6), 567-82.

Pugachev, K. V., Ocran, S. W., Guirakhoo, F., Furby, D., and Monath, T. P. (2002). Heterogeneous nature of the genome of the ARILVAX yellow fever 17D vaccine revealed by consensus sequencing. *Vaccine* 20(7-8), 996-9.

Rey, F. A., Heinz, F. X., Mandl, C., Kunz, C., and Harrison, S. C. (1995). The envelope glycoprotein from tick-borne encephalitis virus at 2 A resolution. *Nature* 375(6529), 291-8.

Roehrig, J. T., Layton, M., Smith, P., Campbell, G. L., Nasci, R., and Lanciotti, R. S. (2002). The emergence of West Nile virus in North America: ecology, epidemiology, and surveillance. *Curr Top Microbiol Immunol* 267, 223-40.

Sambrook, J., Fritsch, E. F., and Maniatis, T. (1989). "Molecular Cloning: A Laboratory Manual," 2nd ed. Cold Spring Harbor Laboratory Press, New York.

Savage, H. M., Ceianu, C., Nicolescu, G., Karabatsos, N., Lanciotti, R., Vladimirescu, A., Laiv, L., Ungureanu, A., Romanca, C., and Tsai, T. F. (1999). Entomologic and avian investigations of an epidemic of West Nile fever in Romania in 1996, with serologic and molecular characterization of a virus isolate from mosquitoes. *Am J Trop Med Hyg* 61(4), 600-11.

Scherret, J. H., Poidinger, M., Mackenzie, J. S., Broom, A. K., Deubel, V., Lipkin, W. I., Briese, T., Gould, E. A., and Hall, R. A. (2001). The relationships between West Nile and Kunjin viruses. *Emerg Infect Dis* 7(4), 697-705.

Shrestha, B., and Diamond, M. S. (2004). Role of CD8+T Cells in Control of West Nile Virus Infection. *J. Virol.* 78(15), 8312-8321.

Smithburn, K. C., Hughes, T. P., Burke, A. V., and Paul, J. H. (1940). A neurotropic virus isolated from the blood of a native of Uganda. *Am J Trop Med Hyg* 20, 471-92.

Tesh, R. B., Arroyo, J., Travassos Da Rosa, A. P., Guzman, H., Xiao, S. Y., and Monath, T. P. (2002). Efficacy of Killed Virus Vaccine, Live Attenuated Chimeric Virus Vaccine, and Passive Immunization for Prevention of West Nile virus Encephalitis in Hamster Model. *Emerg Infect Dis* 8(12), 1392-7.

Wengler, G., and Beato, M. (1979). In vitro translation of 42 S virus-specific RNA from cells infected with the flavivirus West Nile virus. *Virology* 96(2), 516-29.

Wengler, G., Castle, E., Leidner, U., and Nowak, T. (1985). Sequence analysis of the membrane protein V3 of the flavivirus West Nile virus and of its gene. *Virology* 147(2), 264-74.

Wengler, G., and Gross, H. J. (1978). Studies on virus-specific nucleic acids synthesized in vertebrate and mosquito cells infected with flaviviruses. *Virology* 89, 423-437.

WHO. (1998). Requirements for yellow fever vaccine. *WHO Technical Report Series* No. 872, 30-68.

Wu, S. C., and Lee, S. C. (2001). Complete nucleotide sequence and cell-line multiplication pattern of the attenuated variant CH2195LA of Japanese encephalitis virus. *Virus Res* 73(1), 91-102.

Yamshchikov, V. F., Wengler, G., Perelygin, A. A., Brinton, M. A., and Compans, R. W. (2001). An infectious clone of the west nile flavivirus. *Virology* 281(2), 294-304.

Yamshchikov et al., (2004) "An Attenuated West Nile Prototype virus is highly immunogenic and protects against the deadly NY99 strain: a candidate for live WN vaccine development, Virology 330:304-312.

Yamshchikov, V. F., and Compans, R. W. (1995). Formation of the flavivirus envelope: Role of the viral NS2B-NS3 protease. *J. Virol.* 69, 1995-2003.

Zuker, M. (2003). Mfold web server for nucleic acid folding and hybridization prediction. *Nucl. Acids. Res.* 31(13), 3406-3415.

From the foregoing it will be seen that this invention is one well adapted to attain all ends and objectives herein-above set forth, together with the other advantages which are obvious and which are inherent to the invention. Various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A live attenuated homogeneous viral population comprising the WN 1415 (+) RNA virus.

2. A vector comprising DNA encoding infectious (+) RNA molecule encoding the West Nile virus under the control of an eukaryotic promoter, wherein the West Nile virus DNA contains a single intron which is located upstream from the prM signal sequence occurring as the first stretch of hydrophobic amino acids in the WN polyprotein.

3. The vector of claim 2, which comprises SEQ ID NO:1 containing a single intron at position 357.

4. The vector of claim 2, which is a plasmid.

5. The vector of claim 2, wherein the promoter is a cytomegalovirus promoter.

6. The vector of claim 2 designated as pCMVWN.

7. A cell transformed with the vector of claim 2.

8. A vaccine for West Nile virus that protects a subject against West Nile infection comprising a therapeutically effective dose of the virus population of claim 1.

9. The vaccine of claim 8, further comprising a pharmaceutically acceptable carrier.

10. The vaccine of claim 8, wherein the subject is selected from the group consisting of mice, cows, pigs, horses, chickens, cats, and dogs.

11. A method for immunizing a mammal against a West Nile virus comprising the step of administering to the mammal the vaccine of claim 9.

12. The method of claim 11, wherein said administering step is performed intracerebrally, intramuscularly, or intradermally.

13. The method of claim 11, where in the mammal is selected from the group consisting of mice, cows, pigs, horses, chickens, cats, and dogs.

14. A vaccine for West Nile virus that protects a subject against West Nile infection comprising a therapeutically effective dose of the vector of claim 2.

15. The vaccine of claim 14, further comprising a pharmaceutically acceptable carrier.

16. The vaccine of claim 14, wherein the subject is selected from the group consisting of mice, cows, pigs, horses, chickens, cats, and dogs.

17. A method for immunizing a mammal against a West Nile virus comprising the step of administering to the mammal the vaccine of claim 15.

18. The method of claim 17, wherein said administering step is performed intracerebrally, intramuscularly, or intradermally.

19. The method of claim 17, where in the mammal is selected from the group consisting of mice, cows, pigs, horses, chickens, cats, and dogs.

* * * * *